(12) United States Patent
Hang et al.

(10) Patent No.: US 11,896,808 B2
(45) Date of Patent: Feb. 13, 2024

(54) SMART VIAL ADAPTER AND METHOD

(71) Applicant: Becton, Dickinson and Company, Franklin Lakes, NJ (US)

(72) Inventors: Tianqi Hang, Orange, NJ (US); Uzair Siddiqui, Jersey City, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/842,364

(22) Filed: Jun. 16, 2022

(65) Prior Publication Data

US 2022/0305209 A1 Sep. 29, 2022

Related U.S. Application Data

(63) Continuation of application No. 16/051,177, filed on Jul. 31, 2018, now Pat. No. 11,389,596.

(Continued)

(51) Int. Cl.
*G16H 20/17* (2018.01)
*A61J 1/20* (2006.01)
(Continued)

(52) U.S. Cl.
CPC ........ *A61M 5/31546* (2013.01); *A61J 1/2096* (2013.01); *A61M 5/28* (2013.01); *A61M 5/3129* (2013.01); *A61M 5/31566* (2013.01); *G16H 20/17* (2018.01); *G16H 40/63* (2018.01); *G16H 40/67* (2018.01); *A61J 2200/70* (2013.01);
(Continued)

(58) Field of Classification Search
CPC .......... G16H 20/17; A61J 1/2096; A61J 1/201
See application file for complete search history.

(56) References Cited

U.S. PATENT DOCUMENTS

| | | | | |
|---|---|---|---|---|
| 4,813,280 A | * | 3/1989 | Miller, Jr. | ............. G01F 1/6847 73/273 |
| 6,085,588 A | * | 7/2000 | Khadkikar | .............. G01F 1/684 73/204.25 |

(Continued)

FOREIGN PATENT DOCUMENTS

| | | |
|---|---|---|
| AU | 2013219198 B2 | 9/2013 |
| JP | 2004329685 A | 11/2004 |

(Continued)

OTHER PUBLICATIONS

Peter Loftus, Eli Lilly Bets Big on Insulin-Delivery Devices, Nov. 21, 2017, The Wall Street Journal, retrieved from URL: https://www.wsj.com/articles/eli-lilly-bets-big-on-insulin-delivery-devices-1511269200 (3 Pages Total).

*Primary Examiner* — Catharine L Anderson
*Assistant Examiner* — Arjuna P Chatrathi
(74) *Attorney, Agent, or Firm* — Dickinson Wright PLLC (57) ABSTRACT

A smart vial adapter is capable of measuring the dose of a drug that is withdrawn from a vial, measuring the time of a dose capture event, monitoring the vial temperature, measuring the amount of motion or perturbation the vial is subjected to, capturing various other parameters that can provide additional insights associated with the drug or the amount of the dose being drawn from the vial, and communicating the recorded information to a companion application on a computer, smartphone or other device. Related methods are also disclosed and claimed.

13 Claims, 7 Drawing Sheets

Related U.S. Application Data (60) Provisional application No. 62/616,688, filed on Jan. 12, 2018.

(51) Int. Cl.
*A61M 5/31* (2006.01)
*A61M 5/315* (2006.01)
*A61M 5/28* (2006.01)
*G16H 40/67* (2018.01)
*G16H 40/63* (2018.01)
*A61M 5/48* (2006.01)

(52) U.S. Cl.
CPC ..... *A61M 5/482* (2013.01); *A61M 2005/3125* (2013.01); *A61M 2205/3569* (2013.01); *A61M 2205/3584* (2013.01); *A61M 2205/502* (2013.01)

(56) References Cited

U.S. PATENT DOCUMENTS

| | | | |
|---|---|---|---|
| 6,213,996 B1 | 4/2001 | Jepson et al. | |
| 6,813,944 B2* | 11/2004 | Mayer | G01F 1/6845 73/204.26 |
| 6,877,530 B2 | 4/2005 | Osbourne et al. | |
| 7,096,729 B2* | 8/2006 | Repko | G01F 1/6847 73/204.26 |
| 8,286,671 B1 | 10/2012 | Strangis | |
| 8,632,738 B2 | 1/2014 | Giribona et al. | |
| 8,807,131 B1 | 8/2014 | Tunnell et al. | |
| 9,180,257 B2 | 11/2015 | Walters et al. | |
| 9,514,131 B1 | 12/2016 | Bochenko | |
| 11,389,596 B2* | 7/2022 | Hang | A61M 5/28 |
| 2002/0073772 A1* | 6/2002 | Bonne | G01F 1/6842 73/204.11 |
| 2004/0010425 A1 | 1/2004 | Wilkes et al. | |
| 2005/0199647 A1 | 9/2005 | Muto et al. | |
| 2006/0276770 A1 | 12/2006 | Rogers | |
| 2008/0114328 A1 | 5/2008 | Doherty et al. | |
| 2009/0036764 A1 | 2/2009 | Rivas et al. | |
| 2009/0108018 A1 | 4/2009 | Li et al. | |
| 2009/0221890 A1* | 9/2009 | Saffer | A61B 5/742 600/347 |
| 2010/0039252 A1 | 2/2010 | Barkus | |
| 2011/0030845 A1 | 2/2011 | Chong et al. | |
| 2011/0253139 A1 | 10/2011 | Guthrie et al. | |
| 2011/0264069 A1 | 10/2011 | Bochenko | |
| 2012/0095415 A1* | 4/2012 | Sharvit | A61M 39/1011 604/244 |
| 2012/0197184 A1* | 8/2012 | Okuda | A61J 1/2096 141/2 |
| 2012/0246106 A1* | 9/2012 | Atlas | G16H 50/20 700/282 |
| 2012/0323208 A1* | 12/2012 | Bochenko | A61J 1/201 604/404 |
| 2013/0245545 A1* | 9/2013 | Arnold | A61M 5/1723 604/66 |
| 2014/0012511 A1* | 1/2014 | Mensinger | G16H 40/40 702/19 |
| 2014/0127661 A1 | 5/2014 | Yokoi | |
| 2014/0324021 A1 | 10/2014 | Ulrich et al. | |
| 2015/0013810 A1 | 1/2015 | Carrel et al. | |
| 2016/0012205 A1* | 1/2016 | Saint | A61M 5/31528 604/189 |
| 2016/0074587 A1 | 3/2016 | Searle et al. | |
| 2017/0151127 A1 | 6/2017 | Einy et al. | |
| 2017/0232204 A1 | 8/2017 | Knapp et al. | |
| 2017/0286638 A1 | 10/2017 | Searle et al. | |
| 2017/0364660 A1* | 12/2017 | Vigersky | A61M 5/14244 |
| 2018/0036495 A1 | 2/2018 | Searle et al. | |
| 2019/0221301 A1 | 7/2019 | Hang et al. | |

FOREIGN PATENT DOCUMENTS

| | | |
|---|---|---|
| JP | 2006311869 A | 11/2006 |
| JP | 2013025098 A | 2/2013 |
| WO | 2011033788 A1 | 2/2013 |
| WO | 2016040949 A1 | 3/2016 |
| WO | 2018195290 A1 | 10/2018 |

* cited by examiner

SMART VIAL ADAPTER AND METHOD

CROSS-REFERENCE TO RELATED APPLICATION

This application is a continuation of U.S. Nonprovisional application Ser. No. 16/051,177, filed Jul. 31, 2018, which claims the benefit under 35 U.S.C. 119(e) to U.S. provisional application Ser. No. 62/616,688, filed on Jan. 12, 2018, the entire disclosures of said prior applications are incorporated herein in their entirety.

FIELD OF THE INVENTION

The present invention relates generally to vial adapters and dose capture systems. In particular, but not by way of limitation, embodiments of the present invention relate to a smart vial adapter that is capable not only of providing physical access to a drug vial, but also of performing dose capture, condition monitoring and information reporting functions using electronic components contained within the vial adapter. Related methods are also disclosed and claimed.

BACKGROUND OF THE INVENTION

Effective administration of some types of drug injections, particularly in the case of insulin used by diabetics, requires that the drug be kept under proper storage conditions and that a record of all administered doses be kept. While education is offered for home injection patients, most patients still find it challenging to follow the instructions properly on a daily basis. Health care personnel can record dose-related information in a clinical setting, but there is significant overhead associated with capturing this information. It is also difficult to measure and record certain parameters that can affect the safety and efficacy of the drug, such as drug temperature and proper mixing.

Many types of drugs are provided in vials that contain multiple individual doses. The vial is sealed by a rubber septum that can be pierced by a syringe needle when a dose of the drug is drawn from the vial into the syringe in preparation for an injection. If, instead of a needle, the syringe has a blunt cannula or Luer tip that is incapable of piercing the septum, a vial adapter can be used to allow the syringe to access the vial. The vial adapter has a sharp plastic spike or cannula that pierces the septum, and a fluid port, typically in the form of a needleless valve or pre-slit septum, that can be accessed by the blunt cannula or Luer tip of the syringe. The vial adapter can be left in place after it is installed on the vial, allowing multiple doses to be drawn from the vial without repeatedly penetrating the vial septum.

Most vial adapters are entirely mechanical nature, providing only a fluid path between the vial and a syringe, and a secondary seal for the vial. However, the physical presence of the vial adapter on the vial, and its interposition in the fluid path between the vial and the syringe, provides the opportunity for the vial adapter to perform additional functions such as dose capture, condition monitoring and information reporting. The present invention addresses this opportunity by providing a vial adapter with electronic components that allow it to perform these and/or other functions. Related methods are also disclosed and claimed.

SUMMARY OF EMBODIMENTS OF THE INVENTION

In accordance with embodiments of the present invention, a vial adapter is provided that is capable not only of providing physical access to a drug vial, but also of performing dose capture, condition monitoring and information reporting functions using electronic components contained within the vial adapter. These functions can include measuring the dose drawn from the vial, measuring the time of a dose capture event, monitoring the vial temperature, measuring the amount of motion or perturbation the vial is subjected to, capturing various other parameters that can provide additional insights associated with the drug or the amount of the dose being drawn from the vial, and communicating the recorded information to a companion application on a computer, smartphone or other device.

More specifically, one embodiment of the present invention relates to a vial adapter comprising a housing having first and second ends, the first end being open and attachable to a vial, the second end having a fluid port sealed by a penetrable septum; a vial access cannula affixed to the housing and communicating with the fluid port, the vial access cannula being positioned within the open first end of the housing for penetrating the septum of a vial attached to the housing; and electrical components contained within the housing for performing at least one dose capture, condition monitoring or information reporting function with respect to a drug that is contained in or drawn from a vial attached to the housing.

In another embodiment of the present invention, a method for storing and using a drug contained in a vial comprises attaching to the vial an adapter that is capable of performing at least one dose capture, condition monitoring or information reporting function with respect to the drug while the drug is contained in the vial or is drawn from the vial through the adapter; and causing the vial adapter to performing the at least one dose capture, drug monitoring or condition reporting function with respect to the drug while the drug is contained in the vial or is drawn from the vial through the adapter.

BRIEF DESCRIPTION OF THE DRAWINGS

Aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Reference will now be made in detail to embodiments of the present invention, which are illustrated in the accompanying drawings, wherein like reference numerals refer to like elements throughout. The embodiments described and illustrated herein exemplify, but do not limit, the present invention, and the drawings are not necessarily to scale with respect to each other or with respect to actual physical embodiments. Further, it will be understood by one skilled in the art that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as "up", "down", "bottom", "top", "distal" and "proximal" are relative, and are employed to aid illustration, but are not limiting.

Figure 1:
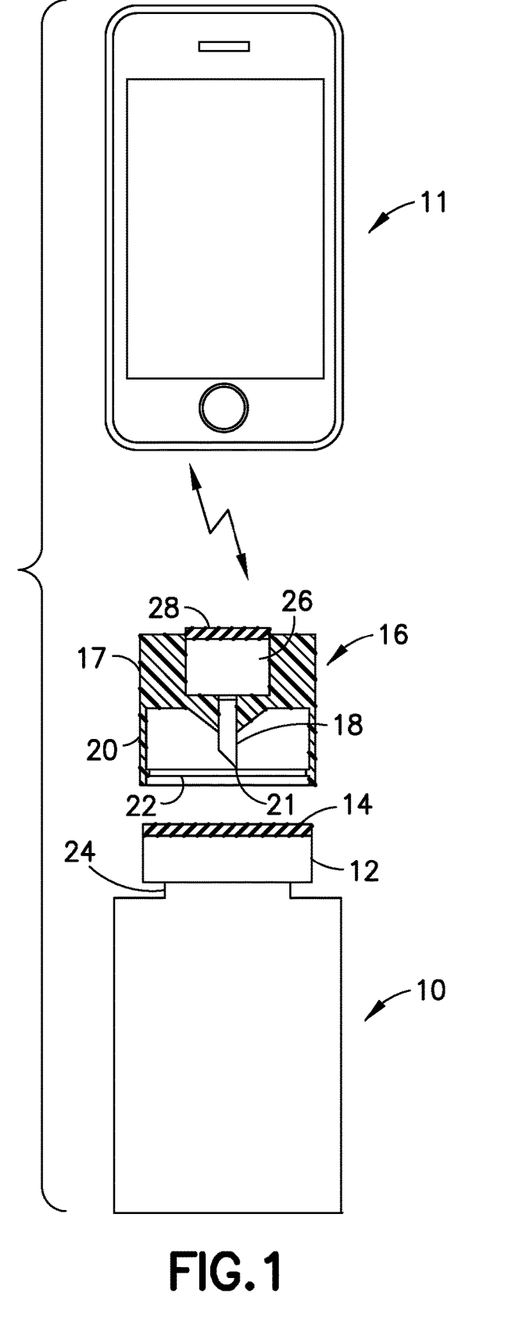
FIG. 1 is a schematic view illustrating a drug vial, a smart vial adapter that is attachable to the drug vial, and a mobile device that wirelessly receives information from the smart vial adapter.
Figure 2:
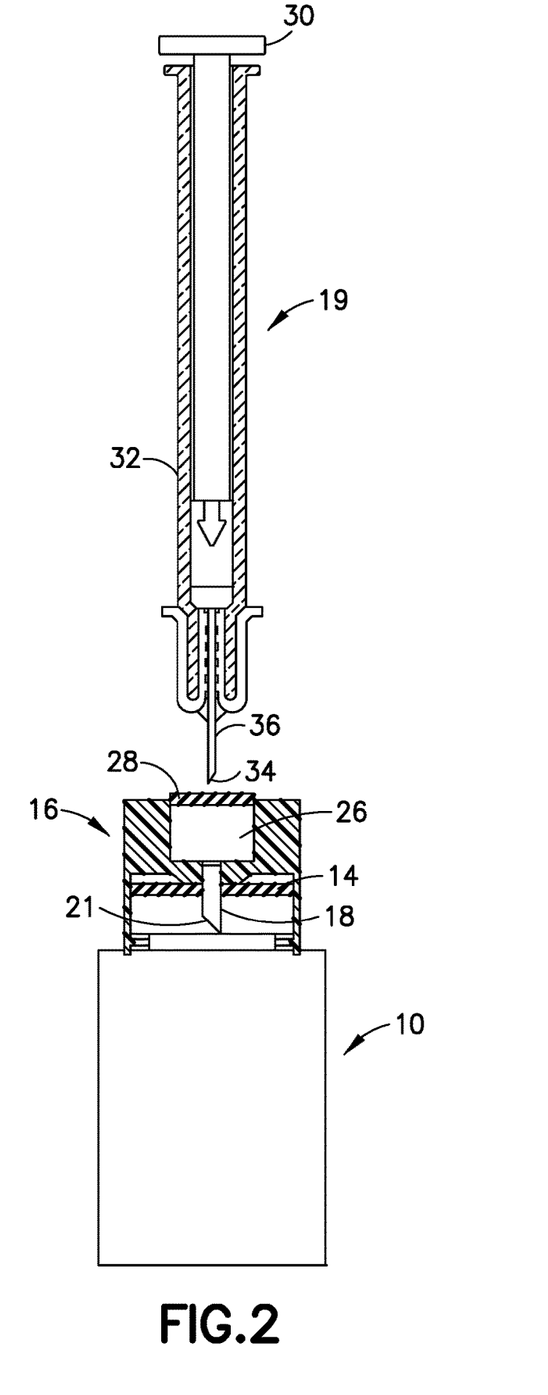
FIG. 2 is a schematic view similar to that of FIG. 1, but with the smart vial adapter attached to the drug vial, a syringe positioned for drawing a dose from the vial through the smart vial adapter, and the mobile device not shown.

FIGS. 1 and 2 are schematic views of the overall combination of elements employed in one embodiment of the present invention. A conventional glass or plastic drug vial 10 containing insulin or another injectable drug in liquid form is sealed by an upper cap 12 having a rubber septum 14. A smart vial adapter 16 that wirelessly communicates a smartphone 11 or other mobile electronic device is attachable to the vial 10. The vial adapter 16 has a cylindrical plastic housing 17 and a vial access cannula in the form of a downwardly projecting, hollow plastic spike 18 with a sharp tip 21. The housing 17 is attachable over the cap 12 to provide fluidic access to the interior of the vial 10 for the purpose of filling a syringe 19.

The vial 10 and vial adapter 16 are shown separated from each other in FIG. 1, as would be the case prior to the vial adapter 16 being installed on the vial 10 or after its removal from the vial 10. In FIG. 2, the vial 10 and vial adapter 16 are shown connected to each other, as they would be during syringe filling. In the connected state, the spike 18 penetrates the vial septum 14 in a fluid-tight manner to communicate with the interior of the vial 10. In addition, an integral lower skirt 20 of the vial adapter housing 17 is received over the vial cap 12, and an inwardly projecting stabilizing ring 22 of the skirt 20 is engaged with an annular groove 24 beneath the cap 12 to provide a releasable snap or detent connection between the vial 10 and vial adapter 16. The plastic material of the vial adapter housing 17 and skirt 20 is sufficiently flexible and resilient to allow for the releasable snap or detent connection between the vial 10 and vial adapter 16.

When the vial 10 and vial adapter 16 are connected to each other as shown in FIG. 2, the syringe 19 can be filled with a dose of the drug contained in the vial 10, via the vial adapter 16, in much the same manner as when a syringe is filled from a vial directly. Initially, the connected vial 10 and vial adapter 16 are inverted to allow the liquid drug to flow from the vial 10 through the inner lumen of the spike 18 into a cylindrical chamber 26 within the housing 17 of the vial adapter 16. A rubber septum 28 seals the chamber 26 to provide sterility and to prevent leakage of air or liquid from (or into) the chamber 26 during syringe filling. Once the chamber 26 is filled, the plunger 30 of the syringe 19 (which is not yet engaged with the vial adapter 16) is pulled back to fill the syringe barrel 32 with an amount of air corresponding to the dose of the drug that is to be withdrawn from the vial 10. The sharp tip 34 of the hollow metal syringe needle 36 is then pushed through the septum 28 of the vial adapter 16, bringing the inner lumen of the hollow needle 36 into fluid communication with the interior of the chamber 26 containing the liquid drug. The plunger 30 of the syringe 19 is then depressed to inject the air into the chamber 26.

Since the connected vial 10 and vial adapter 16 are still inverted at this time, the air will move immediately into the vial 10 and the chamber 26 will refill with the liquid drug. As in the conventional syringe filling procedure (i.e., without the vial adapter 16), the initial injection of air into the vial 10 compensates for the liquid that is to be removed from the vial 10 and thus prevents the formation of a vacuum in the vial 10 when the syringe 19 is filled. After the air injection, and with the connected vial 10 and vial adapter 16 still inverted, the plunger 30 of the syringe 19 is pulled back once again to withdraw the desired amount of liquid drug from the chamber 26 into the syringe barrel 32. As the liquid drug is removed from the chamber 26, the sealed chamber 26 refills with an equal amount of liquid drug from the vial 10 through the inner lumen of the spike 18. The filled syringe 19 can then be used to inject the drug directly into the body of a patient, or into an IV line through a PRN or other type of medical port.

Figure 3:
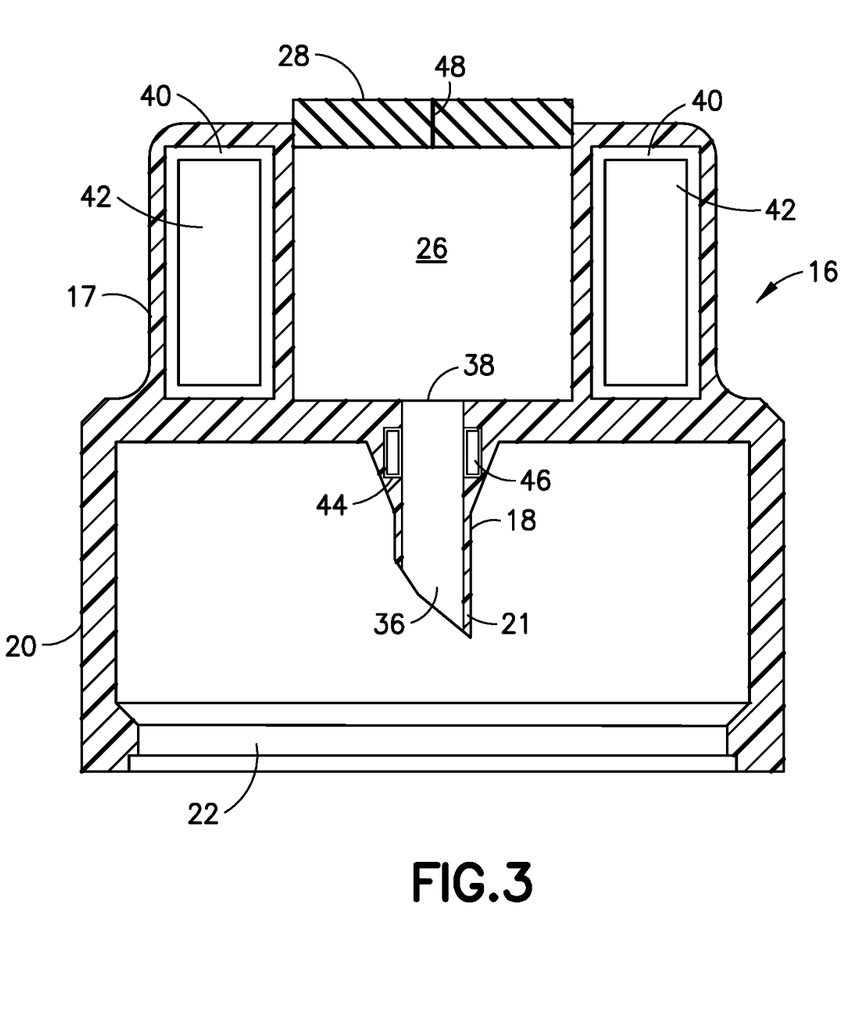
FIG. 3 is a detailed cross-sectional view of the smart vial adapter, shown detached from the drug vial.

FIG. 3 is a detailed cross-sectional view of the smart vial adapter 16, shown detached from the drug vial 10. As illustrated, the chamber 26 communicates with the inner lumen 36 of the spike 18 through an opening 38 at the bottom of the chamber 26, allowing air and liquid to move freely in either direction between the chamber 26 and the interior of the vial 10. Surrounding the chamber 26 is an annular cavity 40 containing various electronic components 42 that allow the smart vial adapter 16 to perform its dose capture, condition monitoring and information reporting functions, as discussed in more detail hereinafter. One or more access doors or plates (not shown) can be provided to allow the components 42 to be installed in the cavity 40 during initial manufacture of the smart vial adapter 16, and to allow for replacement of the battery that powers these components. A smaller annular cavity 44 is formed in surrounding relationship with, and opening into, the inner lumen 36 of the spike 18. This cavity contains one or more electronic flow sensors 46 which are capable of measuring liquid flow within the lumen 36 so that the volume of the liquid drug passing through the lumen 36 during syringe filling can be measured or calculated. This allows the smart vial adapter 16 to perform its dose capture function (i.e., to determine how much of the liquid drug is withdrawn from the vial, and by inference how much of the liquid drug is injected by the user, at a particular time or during a particular interval). The flow sensors 46 are preferably hybrid thermal time of flight (TTOF) flow sensors of the type disclosed in detail in commonly assigned U.S. patent application Ser. No. 15/226,638, filed on Aug. 2, 2016 and published on Feb. 8, 2018 as U.S. Patent Application Publication No. 2018/0036495, which is incorporated herein by reference in its entirety. However, other types of thermal and non-thermal flow sensors can also be used.

During the last part of the syringe filling procedure described above, when the liquid drug is being drawn into the syringe barrel 32 from the chamber 26 of the inverted vial adapter 16, the chamber 26 is completely filled with the liquid drug. As a result, the amount of liquid drug transferred from the chamber 26 into the syringe 19 is replaced by an equal amount of liquid drug that is drawn from the vial 10 into the chamber 26 through the inner lumen 36 of the spike. Since the fluid passing through the lumen 36 flows past the flow sensors 46, this quantity can be calculated based on the measured flow rate and the elapsed time. The calculated quantity represents the dose of the drug that is transferred to the syringe 19 and injected by the user.

FIG. 3 also illustrates that the septum 28, instead of being solid, may be pre-formed with a slit 48 that allows it to be penetrated by a blunt cannula or Luer tip. This may be preferred when the drug that is withdrawn from the vial 10 is intended to be transferred to an IV line through a needleless valve or needleless injection site, rather than being injected into the skin with a needle. In this case the syringe 19 of FIG. 2 is provided with a Luer fitting or blunt cannula, in lieu of the needle 36.

Figure 4:
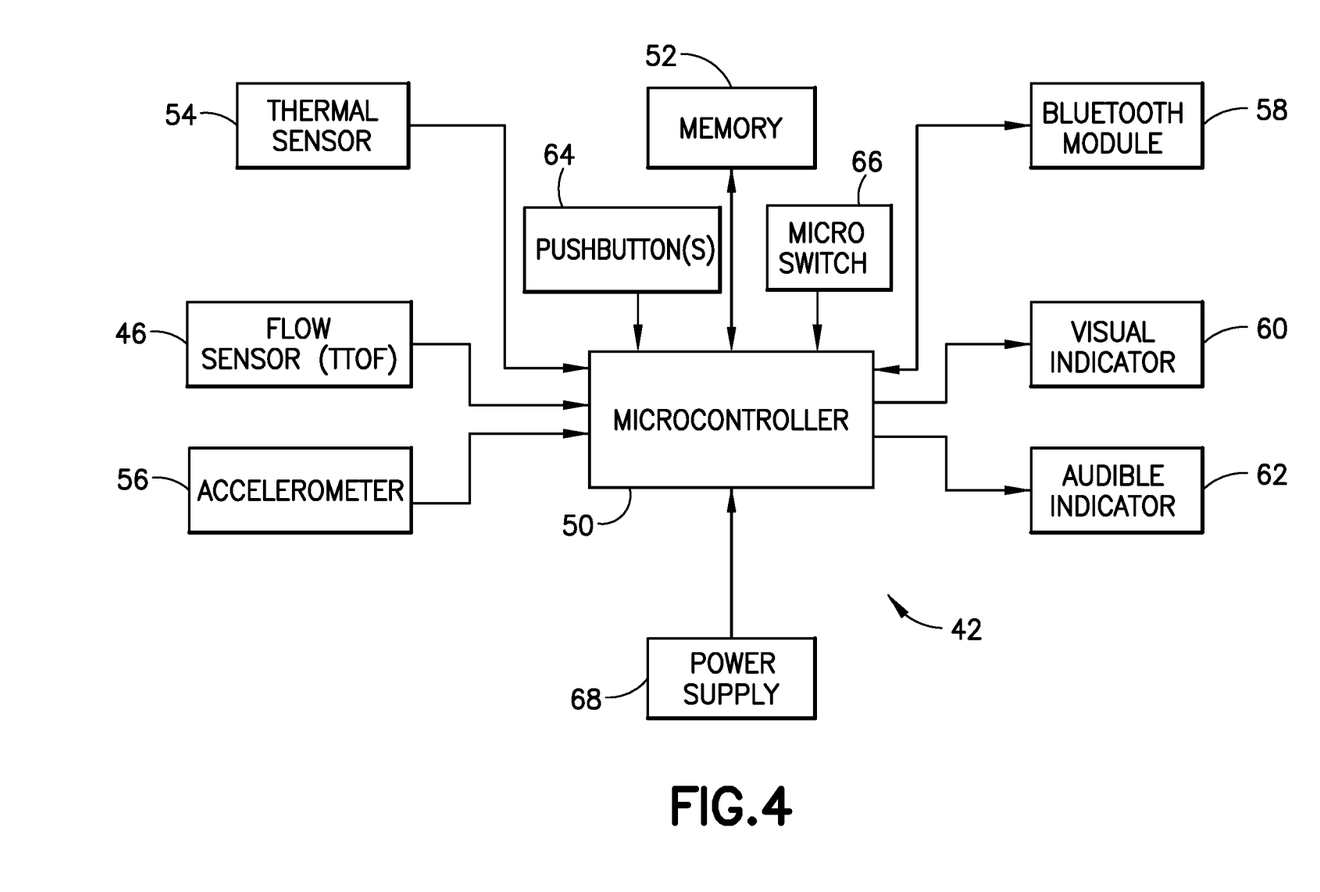
FIG. 4 is a schematic diagram of the electronic components within the smart vial adapter that perform various dose capture, condition monitoring and information reporting functions.

FIG. 4 is a schematic diagram of the electronic components 42 within the smart vial adapter that perform the dose capture function just described, as well as other condition monitoring and information reporting functions. These components include a microcontroller 50 with an internal time-of-day clock, the previously described flow sensor(s) 46, a memory 52 for storing programming and data used by the microcontroller 50, a thermal sensor 54 for detecting the ambient temperature (and by inference the temperature of the vial 10 and its contents), an accelerometer 56 for measuring the amount of motion or perturbation the vial adapter 16 (and by inference the vial 10 and its contents) is subjected to, a Bluetooth module 58 for wirelessly communicating with the smartphone 11 or other external electronic device (such as a computer or tablet), one or more visual indicators 60 such as differently colored LEDs, one or more audible or tactile indicators 62 such as beepers, buzzers, speakers or vibrating devices, one or more pushbuttons 64, and a microswitch 66 that senses the initial connection of the vial adapter 16 to the vial 10. A power supply 68, typically in the form of a replaceable or rechargeable DC battery and suitable voltage regulating circuitry, supplies power to the microcontroller 50 and to any of the other components of FIG. 4 that require electrical power.

Figure 5:
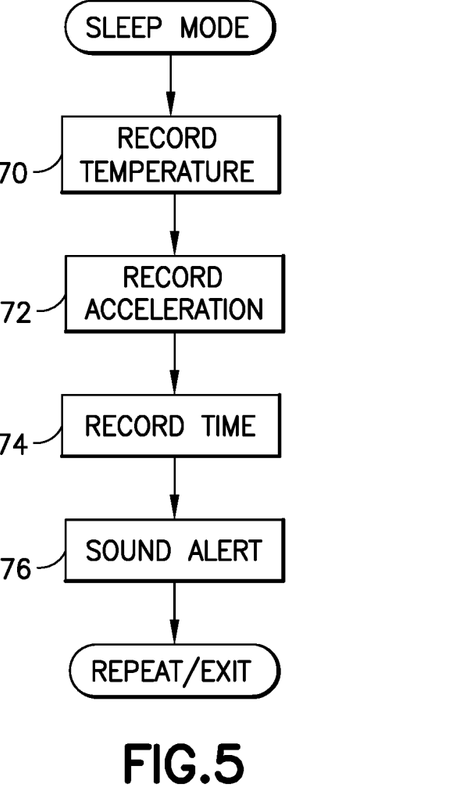
FIGS. 5 and 6 are flow charts of the operations performed by the smart vial adapter while operating in its sleep and active modes, respectively.

FIG. 5 is a flow chart of the operations performed by the microcontroller 50 while the smart vial adapter 16 is operating in its sleep mode. This is the normal or default operating mode of the vial adapter 16 when it is not being used. In step 70, the microcontroller 50 records the ambient temperature using the thermal sensor 54 and stores the recorded value in the memory 52. In step 72, the microcontroller 50 records any motion or agitation that the vial adapter 16 may be undergoing, using the accelerometer 56, and stores the recorded value in the memory 52. In step 74, the microcontroller 50 records the current time of day and stores the recorded value in the memory 52 with the associated temperature and motion readings. The time, temperature and motion readings provide time-temperature and agitation data that can be used to verify that the drug has been stored at the proper temperature, that is has been properly mixed prior to use, and that is has not expired. In step 76, an alert is sounded using the visual and/or audible indicators 60, 62 either when it time for the user to receive a dose of the drug, or when a condition is detected that requires intervention by the user. Such conditions can include a temperature that is too high or too low over an extended period of time, a lack of movement of the vial adapter 16 for a sufficient amount of time that the drug may require agitation or mixing before use, or expiration of the drug in the vial 10. The steps 70-76 are performed repeatedly, at a predetermined sampling frequency (e.g., once per minute) while the smart vial adapter 16 is operating in its sleep mode.

Figure 6:
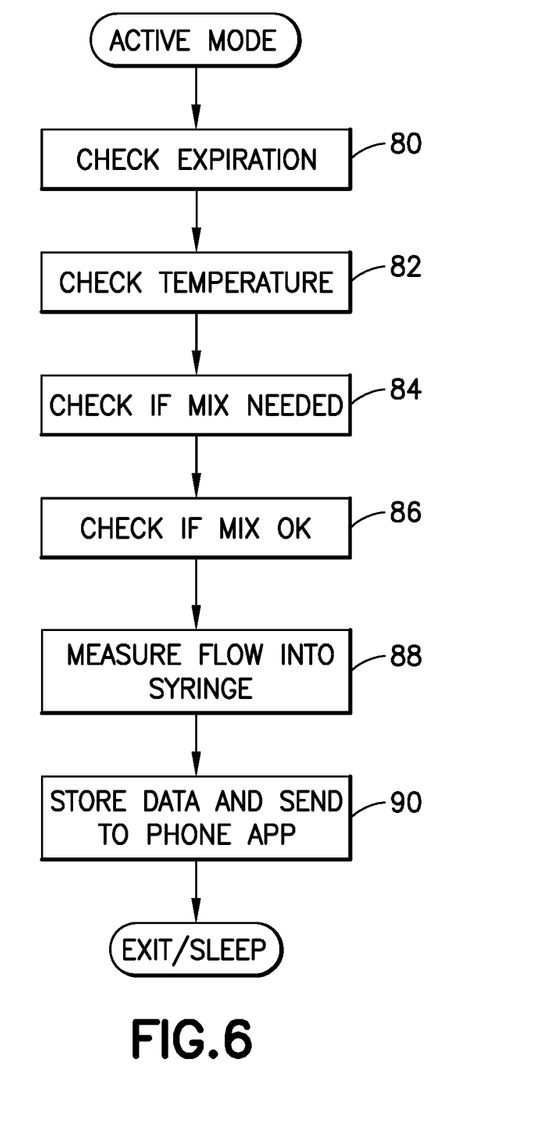

FIG. 6 is a flow chart of the operations performed by the microcontroller 50 while the smart vial adapter 16 is operating in its active mode. This is the operating mode in which the vial adapter 16 is placed, either by an intentional user input (e.g., depression of one of the pushbuttons 64), or by a sensed condition such as sudden movement (detected by the accelerometer 56), when the vial adapter is about to be used for an injection. In step 80, a check is made to determine if the drug has expired by comparing the current time with a predetermined start time. The predetermined start time can be defined, for example, by a user input such as depression of another one of the pushbuttons 64, or by the microswitch 66 sensing the initial connection of the vial adapter 16 to the vial 10. In steps 82 and 84, checks are made to determine if the drug is at the proper temperature for use and (based on prior agitation history) whether further mixing of the drug is needed. If further mixing is needed, the user is alerted to this using the visual and/or audible indicators 60, 62, and in step 86, a check is made to confirm that the user has in fact provided adequate mixing. The user then proceeds to fill the syringe 19 from the vial adapter 16 using the procedure previously described. In step 88, the microcontroller 50 calculates the dose that is drawn from the chamber 26 into the syringe 19 (with compensation for any dead space within the syringe) using the data from the flow sensor(s) 46. If desired, the audible indicator 62 can be made to produce beeps of increasing frequency and/or intensity as the draw nears a preset volume. In step 90, the calculated dose volume is stored in the memory 52, along with the corresponding temperature, time of day, and any other desired information. If an active Bluetooth connection is detected, this dose capture data is also transmitted to the smartphone application using the Bluetooth module 58. The vial adapter then re-enters the sleep mode until the next dosing event is detected. Each time that a dose is drawn from the vial 10 through the vial adapter 16, the active mode of FIG. 6 is re-entered and the steps 80-90 are repeated.

Figure 7:
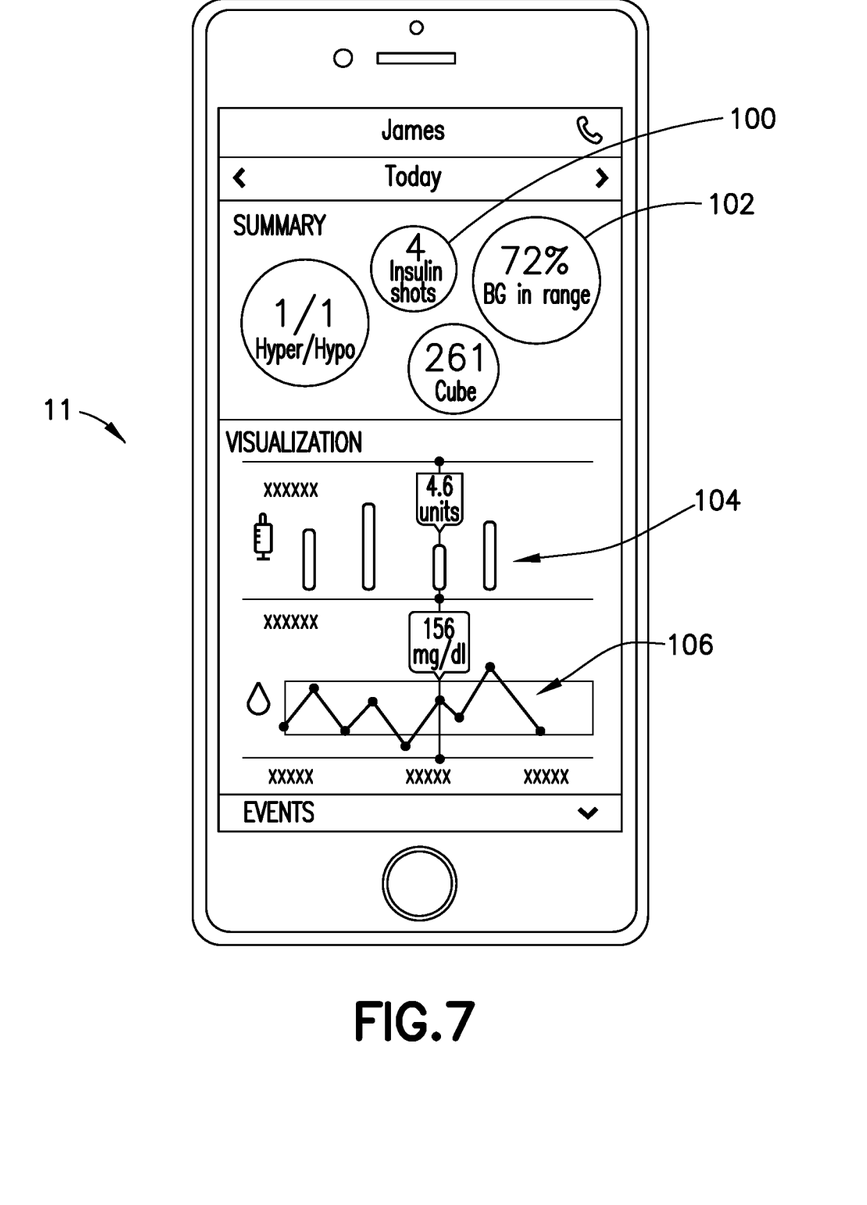
FIGS. 7-9 are exemplary screen displays that can be produced by a mobile device that is programmed with a software application associated with the smart vial adapter.
Figure 8:
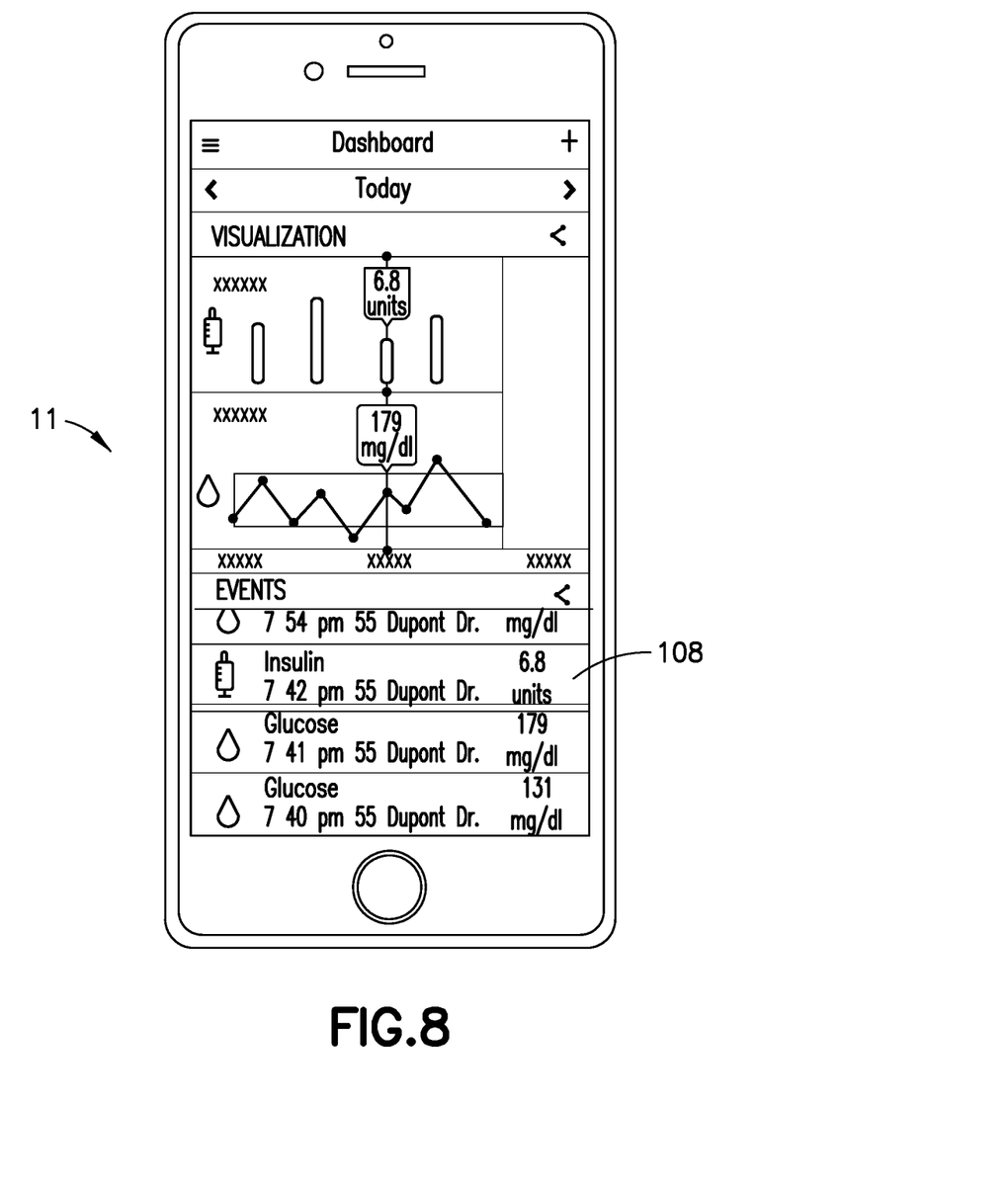
Figure 9:
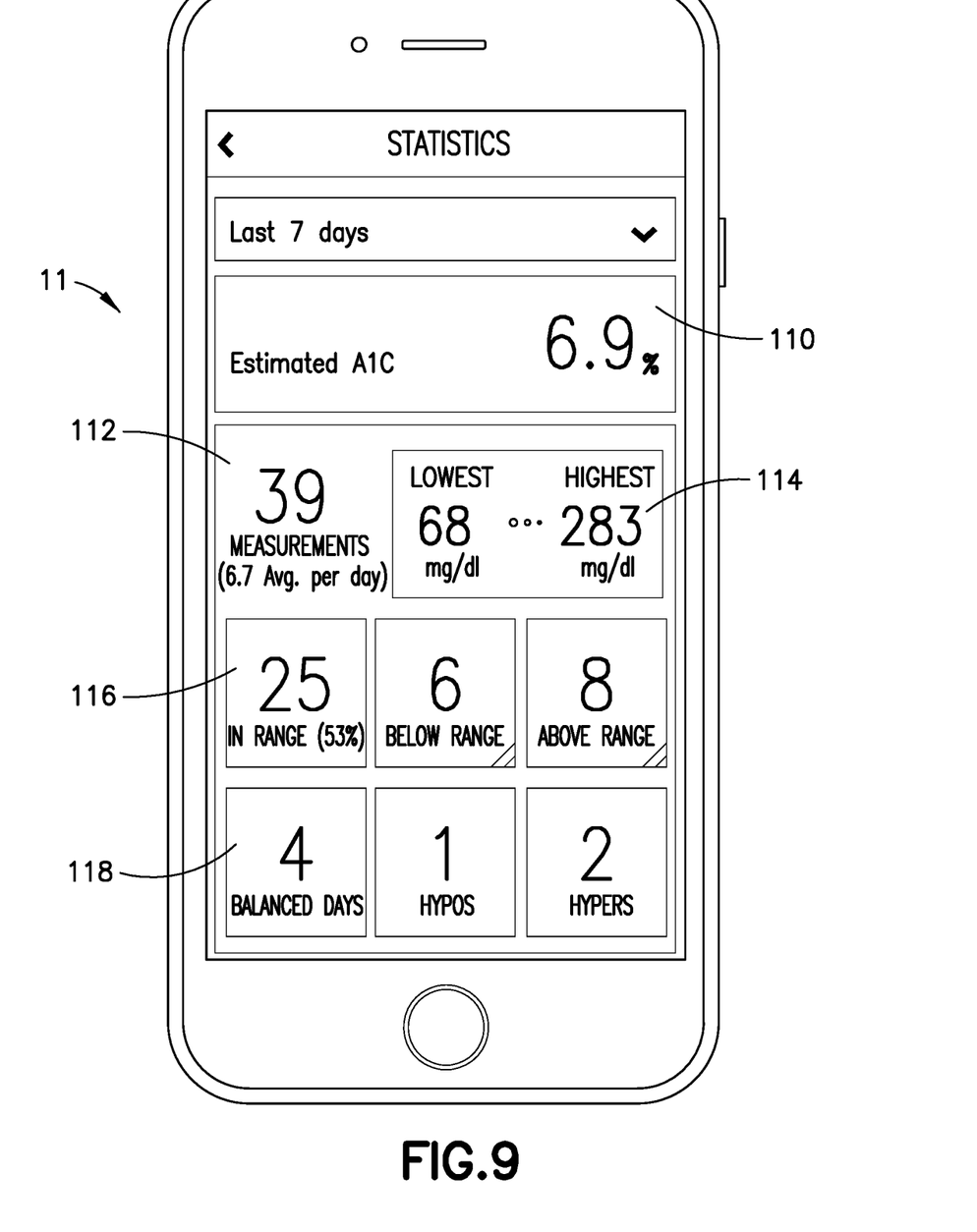

FIGS. 7-9 are exemplary screen displays that can be produced on a smartphone 11 or other mobile device that is programmed with a software application associated with the smart vial adapter 16. In the illustrated example, the drug being administered is insulin and the user is assumed to have entered or imported his or her blood glucose measurements into the smartphone application for processing along with the measured dose capture data from the vial adapter 16. In FIG. 7, the displayed information includes the user's statistics for the current day, including the number 100 of injections administered, the percentage 102 of blood glucose measurements within a desired range, a bar chart 104 showing the amount of insulin (e.g., the number of units or the volume in milliliters) administered in each injection, and a line chart 106 showing blood glucose level over time. In FIG. 8, an events panel 108 is added to the display to pair blood glucose measurements with injection events. In FIG. 9, the user's statistics over a 7-day period are displayed. These include estimated A1c level 110 based on injection and glucose data for the 7-day period, the total number and daily average 112 of blood glucose measurements over the 7-day period, the number 116 of in-range, below-range and above-range blood glucose measurements making up the 7-day total, and the number 118 of balanced, hypoglycemic and hyperglycemic days within the 7-day period.

In an alternative embodiment that is not illustrated in the drawings, an electrically powered air pump and air filter may incorporated into the housing 17 of the vial adapter 16 to force filtered air into the vial 10 before a dose of the liquid drug is drawn into the syringe 19 from the vial 10. This eliminates the need for the user to manually perform this initial step using the syringe 19. Additional details concerning this embodiment can be found in a commonly assigned U.S. patent application of Tianqi Hang and Uzair Siddiqui filed on Jul. 31, 2018 and entitled "Medication Dispensing System", which is incorporated herein by reference in its entirety.

Although only a few embodiments of the present invention have been shown and described, the present invention is not limited to the described embodiments. Instead, it will be appreciated by those skilled in the art that changes may be made to these embodiments without departing from the scope of the invention. In addition, any of the embodiments, features and/or elements disclosed herein may be combined with one another to form various additional combinations not specifically disclosed, as long as the embodiments, features and/or elements being combined do not contradict each other. All such changes and combinations are considered to be within the scope of the invention as defined by the appended claims and their equivalents.

What is claimed is:

1. A system including an electronic device connected to a vial adapter, the system comprising:
    the vial adapter including:
        a housing having a sensor cavity, a first end configured to be attached to a vial and a second end having a fluid port sealed by a penetrable septum;
        a vial access cannula having an internal lumen, the vial access cannula affixed to the housing and communicating with the fluid port, the vial access cannula being positioned within the first end of the housing for penetrating a septum of a vial attached to the housing, the sensor cavity of the vial adapter being open to the internal lumen;
        electrical components contained within the housing for performing at least one of dose capture, condition monitoring and information reporting function with respect to a drug that is contained in or drawn from a vial attached to the housing; and
        a microcontroller communicating with the electrical components to provide instructions and record data; and
    the electronic device including:
        a display communicating with the microcontroller of the vial adapter to display the data recorded based on the instructions received.

2. The system of claim 1, wherein the vial adapter further comprises:
    an electronic flow sensor; wherein
    the electronic flow sensor surrounds the internal lumen of the vial access cannula for sensing fluid flow within the vial access cannula.

3. The system of claim 2, wherein the electronic flow sensor of the vial adapter is disposed in the sensor cavity of the housing.

4. The system of claim 1, wherein
    the housing of the vial adapter includes an internal fluid chamber between the fluid port and the vial access cannula, the internal fluid chamber being sealed by the septum and communicating with the internal lumen of the vial access cannula through an opening that allows air and liquid to move freely in either direction between the internal fluid chamber and an interior of the vial through the internal lumen of the vial access cannula.

5. The system of claim 1, wherein the electrical components contained within the vial adapter include one or more of a flow sensor, a thermal sensor, an accelerometer, a microcontroller, a visual indicator, an audible indicator and a Bluetooth® wireless module.

6. The vial adapter of claim 1, wherein the electrical components of the vial adapter are received in an internal cavity of the housing that is adjacent to an internal fluid chamber.

7. The system of claim 1, wherein
    the housing of the vial adapter includes an electrically powered air pump and an air filter to force filtered air into the vial before a dose of the drug is drawn into a syringe from the vial; and
    the electronic device is configured to remotely and wirelessly communicate with the vial adapter.

8. The system of claim 1, wherein the display of the electronic device presents at least one of a number of injections administered, a percentage of blood glucose measurements within a desired range, a bar chart showing an amount of insulin administered in each injection, and a line chart showing blood glucose level over time.

9. The system of claim 1, wherein the display of the electronic device presents an events panel to pair the blood glucose measurements with injection events.

10. The system of claim 1, wherein the display of the electronic device presents a user's statistics over a 7-day period.

11. The system of claim 10, wherein the display of the electronic device presents the user's statistics over the 7-day period includes one of estimated A1c level based on injection and glucose data for the 7-day period, a total number and daily average of blood glucose measurements over the 7-day period, a number of in-range, below-range and above-range blood glucose measurements making up the 7-day total, and a number of balanced, hypoglycemic and hyperglycemic days within the 7-day period.

12. The system of claim 1, wherein the display of the electronic device presents at least one of the following: (a) the number of doses withdrawn from the vial during a predetermined period of time; (b) the dosage amount for each of a plurality of doses withdrawn from the vial during a predetermined period of time; (c) dosage events paired with contemporaneously measured physiological data; and (d) estimated or projected physiological data based on dosage history.

13. The system of claim 1, wherein the electronic device includes a computer, a smartphone or other mobile device that is programmed with a software application for processing the data and providing a user output, the electronic device is separate and independent from the vial adapter.

* * * * *